US011042021B2

(12) United States Patent
Aruga et al.

(10) Patent No.: US 11,042,021 B2
(45) Date of Patent: Jun. 22, 2021

(54) IMAGE PICKUP APPARATUS AND ENDOSCOPE APPARATUS

(71) Applicant: OLYMPUS CORPORATION, Tokyo (JP)

(72) Inventors: Junko Aruga, Sagamihara (JP); Susumu Takahashi, Iruma (JP)

(73) Assignee: OLYMPUS CORPORATION, Tokyo (JP)

( * ) Notice: Subject to any disclaimer, the term of this patent is extended or adjusted under 35 U.S.C. 154(b) by 393 days.

(21) Appl. No.: 15/973,712

(22) Filed: May 8, 2018

(65) Prior Publication Data

US 2018/0341100 A1  Nov. 29, 2018

(30) Foreign Application Priority Data

May 29, 2017  (JP) .............................. JP2017-105551

(51) Int. Cl.
| | | |
|---|---|---|
| G02B 23/24 | (2006.01) | |
| H04N 5/235 | (2006.01) | |
| A61B 1/00 | (2006.01) | |
| A61B 1/05 | (2006.01) | |
| H04N 13/239 | (2018.01) | |
| G02B 23/26 | (2006.01) | |
| H04N 5/225 | (2006.01) | |

(52) U.S. Cl.
CPC ........ G02B 23/243 (2013.01); A61B 1/00096 (2013.01); A61B 1/00101 (2013.01); A61B 1/00193 (2013.01); A61B 1/05 (2013.01); G02B 23/2484 (2013.01); H04N 5/2353 (2013.01); H04N 13/239 (2018.05); *G02B 23/26* (2013.01); *H04N 2005/2255* (2013.01)

(58) Field of Classification Search
CPC .. G02B 23/243; G02B 23/2484; G02B 23/26; G02B 23/24; G02B 23/2407; G02B 23/2415; G02B 23/2423; G02B 23/2446; H04N 13/239; H04N 5/2353; H04N 2005/2255; A61B 1/00096; A61B 1/00101; A61B 1/00193; A61B 1/05
See application file for complete search history.

(56) References Cited

U.S. PATENT DOCUMENTS

2010/0208046 A1* 8/2010 Takahashi .............. A61B 1/042
348/65

FOREIGN PATENT DOCUMENTS

| JP | 2010-128354 A | 6/2010 |
|---|---|---|
| JP | 2016-085414 A | 5/2016 |

* cited by examiner

*Primary Examiner* — Stephone B Allen
*Assistant Examiner* — Adam W Booher
(74) *Attorney, Agent, or Firm* — Scully, Scott, Murphy & Presser, P.C.

(57) ABSTRACT

An endoscope apparatus includes two optical path forming optical systems, an image forming optical system, two convex power sections including a convex section, provided in the two optical path forming optical systems, and disposed so as to emit emitted light from the two optical path forming optical systems to the image forming optical system, and an aperture member including two openings configured to transmit the light emitted from the two convex power sections. The centers of the two openings are respectively located on the optical axis side of the image forming optical system with respect to the two optical axes of the two optical path forming optical systems.

11 Claims, 6 Drawing Sheets

IMAGE PICKUP APPARATUS AND ENDOSCOPE APPARATUS

CROSS REFERENCE TO RELATED APPLICATION

This application claims benefit of Japanese Application No. 2017-105551 filed in Japan on May 29, 2017, the contents of which are incorporated by this reference.

BACKGROUND

1. Technical Field

The present invention relates to an image pickup apparatus and an endoscope apparatus using the image pickup apparatus, and more particularly, to an image pickup apparatus and an endoscope apparatus having first and second optical path forming optical systems.

2. Background Art

Conventionally, endoscopes are widely used in an industrial field and a medical field. In each endoscope, light incident through an observation window from an object is made incident on a light receiving surface of an image pickup device through an observation optical system, and an object image is projected onto an image pickup surface of the image pickup device. The image pickup device photoelectrically converts the object image projected onto the image pickup surface and outputs the object image as an image pickup signal. An endoscope image is generated from the image pickup signal.

Furthermore, endoscopes including two optical systems having parallax capable of performing so-called stereo measurement or stereo observation exist. Light beams passing through the two optical paths form images on the image pickup surface of the image pickup device. For example, as disclosed in Japanese Patent Application Laid-Open Publication No. 2016-85414, two schemes exist: one in which light passing through one optical path and light passing through the other optical path form images in two different regions on the image pickup surface of the image pickup device, and the other in which the two light beams form images in an identical, that is, a common region on the image pickup surface of the image pickup device. In the case of the scheme in which the two light beams from the two optical paths form images in a common image pickup surface of one image pickup device, optical path switching means is provided which operates so as to alternately project the light beams from the two optical paths.

In order to improve measurement accuracy or the like, a parallax amount is preferably increased, but increasing the parallax amount requires an interval between two openings constituting apertures to be increased.

SUMMARY

An image pickup apparatus according to one aspect of the present invention includes a first optical path forming optical system configured to form a first optical path, a second optical path forming optical system configured to form a second optical path, an image forming optical system disposed so as to receive emitted light from the first optical path forming optical system and emitted light from the second optical path forming optical system, a first convex power section including a convex portion, provided in the first optical path forming optical system and disposed so as to emit the emitted light from the first optical path forming optical system toward the image forming optical system, a second convex power section including a convex portion, provided in the second optical path forming optical system and disposed so as to emit the emitted light from the second optical path forming optical system toward the image forming optical system, and an aperture member including a first opening configured to transmit the light emitted from the first convex power section and a second opening configured to transmit the light emitted from the second convex power section with a center of the first opening being located on an optical axis side of the image forming optical system with respect to a first optical axis of the first optical path forming optical system and a center of the second opening being located on an optical axis side of the image forming optical system with respect to a second optical axis of the second optical path forming optical system.

An endoscope apparatus according to an aspect of the present invention includes the image pickup apparatus of the present invention.

DETAILED DESCRIPTION OF PREFERRED EMBODIMENT(S)

Figure 1:
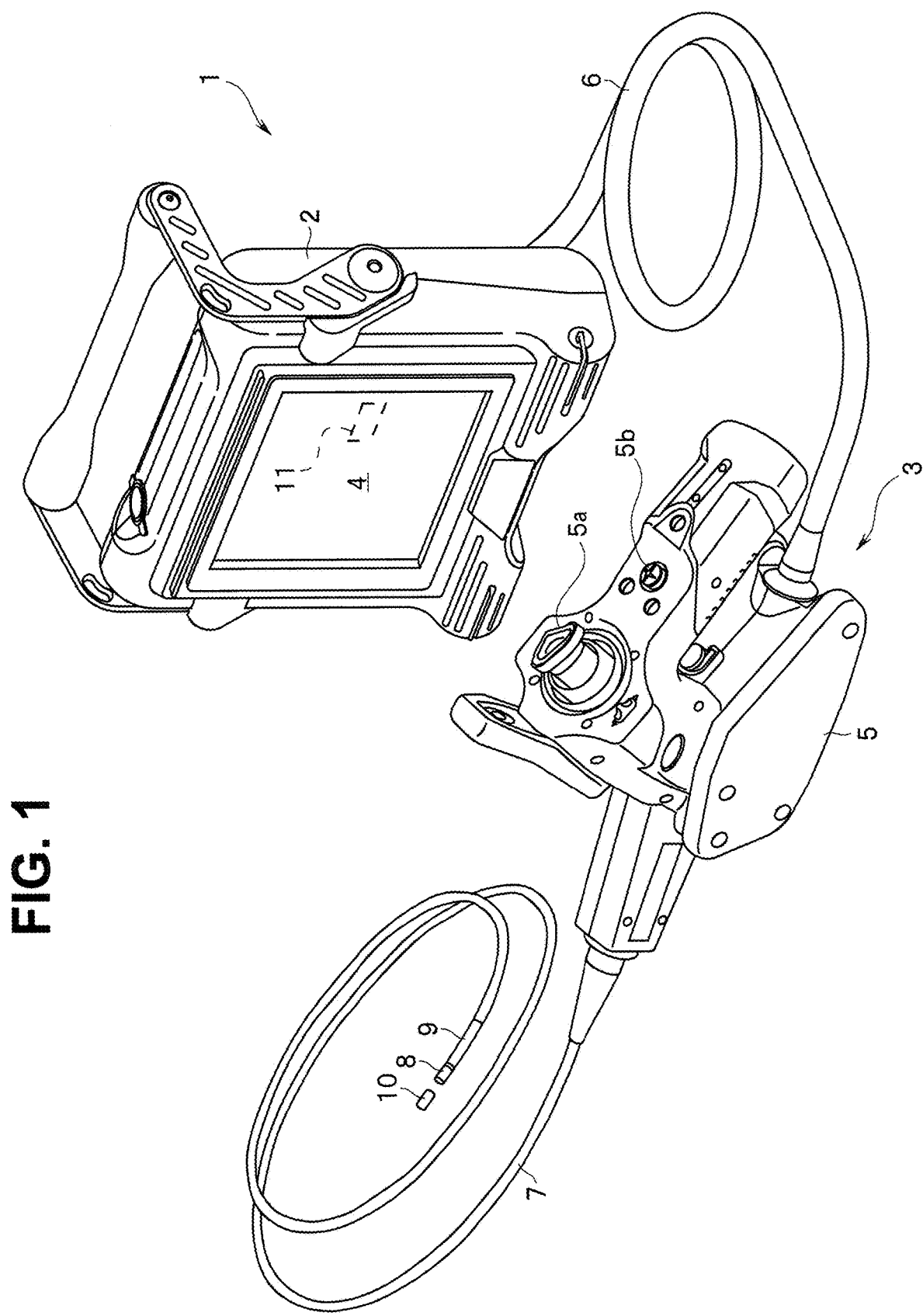
FIG. 1 is an appearance configuration diagram of an endoscope according to a first embodiment of the present invention.

Hereinafter, embodiments of the present invention will be described with reference to the accompanying drawings.

Note that in the respective drawings used in the following description, respective components are shown in scales varying from one component to another to illustrate the respective components in such sizes that they are recognizable in the drawings, and so, the present invention is not exclusively limited to a quantity of the components, shapes of the components, a size ratio among the components and relative positional relationships among the components illustrated in the drawings.

First Embodiment (Overall Configuration)

FIG. 1 is an appearance configuration diagram of an endoscope according to the present embodiment.

As shown in FIG. 1, an endoscope apparatus 1 includes a body section 2 which is a main unit, and a scope unit 3 connected to the body section 2. The body section 2 includes a liquid crystal display section (hereinafter abbreviated as an "LCD") 4 as a display apparatus configured to display an endoscope image, an operation menu or the like. The LCD 4 is a display section configured to display an endoscope image. The LCD 4 is provided with a touch panel.

The scope unit 3 includes an operation portion 5 connected to the body section 2 via a universal cable 6 which is a connection cable and an insertion portion 7 including a flexible insertion tube and connected to the operation portion 5. The scope unit 3 is configured to be attachable/detachable to/from the body section 2. A distal end portion 8 of the insertion portion 7 incorporates an image pickup unit which is an image pickup apparatus and which will be described later. The image pickup unit is constructed of an image pickup device, for example, a CCD image sensor or a CMOS image sensor, and an image pickup optical system such as a lens disposed on a light receiving surface side which is an image pickup surface of the image pickup device.

The image pickup device includes a color filter section, and a pattern of each color filter or the like of the color filter section is, for example, a pattern of a Bayer array.

A bending portion 9 is provided on a proximal end side of the distal end portion 8. An optical adapter 10 can be attached to the distal end portion 8. The operation portion 5 is provided with various operation buttons such as a freeze button and a recording instruction button (hereinafter referred to as an "REC button").

A user can pick up an image of an object, record a still image or the like by operating the various operation buttons of the operation portion 5. The operation portion 5 is further provided with joysticks 5a and 5b. The user can bend the bending portion 9 by operating the joystick 5a.

Image data of an endoscope image acquired by picking up an image is inspection data of an inspection target and is recorded in a memory card 11 which is a recording medium attachable/detachable to/from the body section 2.

The optical adapter 10 is a stereo measurement optical adapter and by attaching the optical adapter 10 to the distal end portion 8 of the insertion portion 7, the endoscope apparatus 1 can exhibit a stereo measurement function and a stereo observation function.

The optical adapter 10 includes a lens group configured to form two optical paths for stereo measurement or stereo observation. That is, the optical adapter 10 includes two optical path forming optical systems for two optical paths having parallax. An image pickup device 35 (see FIG. 2) is disposed at an image forming position of the two optical path forming optical systems. Two optical systems at left and right are pupil decentered optical systems, which have no emission pupil position on the central axis orthogonal to a light receiving surface of the image pickup device, that is, decentered.

The two emission pupil positions of the two optical path forming optical systems are set at positions mutually decentered from the central axes orthogonal to the light receiving surface of the image pickup device.

(Configuration of Image Pickup Optical System)

Figure 2:
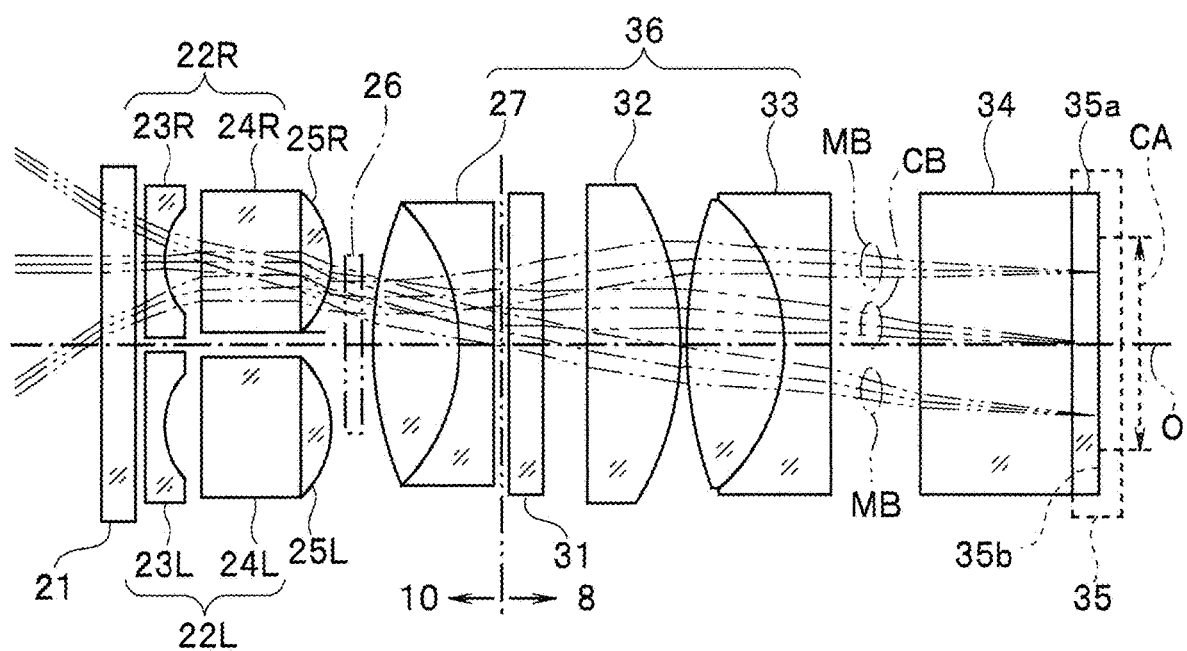
FIG. 2 is a configuration diagram of an optical system of a distal end portion 8, with an optical adapter 10 attached at a distal end according to the first embodiment of the present invention.

FIG. 2 is a configuration diagram of the optical system of the distal end portion 8 with the optical adapter 10 attached at the distal end.

A cover glass 21 is provided at the distal end of the optical adapter 10. Right and left objective optical systems, that is, a right eye optical system 22R and a left eye optical system 22L are arranged inside the optical adapter 10 behind the cover glass 21.

The right eye optical system 22R includes a plano-concave lens 23R and a plano-convex lens 24R in order from the distal end. A proximal end portion of the plano-convex lens 24R constitutes a convex power section 25R.

The left eye optical system 22L includes a plano-concave lens 23L and a plano-convex lens 24L in order from the distal end. A proximal end portion of the plano-convex lens 24L constitutes a convex power section 25L.

The optical adapter 10 includes the right eye optical system 22R as a first optical path forming optical system that forms a first optical path and the left eye optical system 22L as a second optical path forming optical system that forms a second optical path.

Furthermore, the convex power section 25R has a convex portion, is provided inside the right eye optical system 22R which is the first optical path forming optical system and disposed so as to emit the emitted light from the first optical path forming optical system toward an image forming optical system 36. The convex power section 25L also has a convex portion, is provided inside the left eye optical system 22L which is the second optical path forming optical system and disposed so as to emit the emitted light from the second optical path forming optical system toward the image forming optical system 36.

The plano-concave lens 23R is provided on an incident light side of the right eye optical system 22R which is the first optical path forming optical system and is an optical element having a concave surface. The plano-concave lens 23L is provided on an incident light side of the left eye optical system 22L which is the second optical path forming optical system and is an optical element having a concave surface.

To improve assembling efficiency of each optical path forming optical system, the optical axis of the plano-concave lens 23R is aligned with the optical axis of the plano-convex lens 24R, and the optical axis of the plano-concave lens 23L is aligned with the optical axis of the plano-convex lens 24L.

Note that the plano-convex lenses 24R and 24L may also be concave-convex lenses.

A mechanical shutter 26 and a bonded convex lens 27 formed of a plurality of lenses are arranged in order from the distal end toward the proximal end on the proximal end side of the right eye optical system 22R and the left eye optical system 22L in the optical adapter 10.

A cover glass 31, a plano-convex lens 32, and a bonded convex lens 33 formed of a plurality of lenses are arranged in order from the distal end in the distal end portion 8. An image pickup device 35 to which a protective glass section 34 formed of a plurality of glass sheets is fixed is arranged on a proximal end side of the bonded convex lens 33.

The bonded convex lens 27, the plano-convex lens 32 and the bonded convex lens 33 constitute an image forming optical system 36 common to the right eye optical system 22R and the left eye optical system 22L.

A luminous flux emitted from the right eye optical system 22R and light emitted from the left eye optical system 22L pass through the two openings of the mechanical shutter 26, respectively, are made incident on the image forming optical system 36 and emitted toward a common image pickup region on the image pickup surface of the image pickup device 35.

That is, the image forming optical system 36 is disposed so as to make incident the emitted light from the right eye optical system 22R which is the first optical path forming optical system and the emitted light from the left eye optical system 22L which is the second optical path forming optical system. The image pickup device 35 is arranged at an image forming position of the light emitted from the image forming optical system 36.

Note that the bonded convex lens 27 may be formed of a lens or the like that bonds a plano-convex lens and a concave-flat lens together, a proximal end side of the adapter of which is flat. The cover glass may be provided in the optical adapter 10 so as to be disposed between the optical adapter 10 and the distal end portion 8.

The mechanical shutter 26 is configured to operate so as to cause the light passing through the right eye optical system 22R and the light passing through the left eye optical system 22L to alternately radiate onto the image pickup device 35. Thus, the image pickup device 35 alternately receives the light passing through the right eye optical system 22R and the light passing through the left eye optical system 22L. The light passing through the right eye optical system 22R and the light passing through the left eye optical system 22L respectively form images in a common image pickup region on the image pickup surface of the image pickup device 35.

As described above, the mechanical shutter 26 is a shutter arranged between the two optical systems of the right eye optical system 22R and the left eye optical system 22L, and the image forming optical system 36. The image forming optical system 36 is configured to cause the emitted light from the right eye optical system 22R and the emitted light from the left eye optical system 22L to form images in a common region of the image pickup surface of the image pickup device 35. The mechanical shutter 26 operates so as to cause the emitted light from the right eye optical system 22R and the emitted light from the left eye optical system 22L to be alternately radiated onto the common region.

Note that the mechanical shutter 26 is arranged between the two optical systems of the right eye optical system 22R and the left eye optical system 22L, and the image forming optical system 36, but the mechanical shutter 26 may be disposed at any place if it is located on the proximal end side of the convex power sections 25R and 25L in the optical adapter 10.

A cover glass 35a is also provided on the image pickup surface of the image pickup device 35. The protective glass section 34 is arranged on the cover glass 35a.

An effective pixel region CA is set at a center of an image pickup surface 35b of the image pickup device 35.

Note that FIG. 2 illustrates only optical paths of a central luminous flux CB and two off-axis luminous fluxes MB of luminous fluxes passing through the right eye optical system 22R. The central luminous flux CB is a luminous flux passing through the aperture from a view center of the light from the object. The off-axis luminous fluxes MB are luminous fluxes other than the central luminous flux CB.

Figure 3:
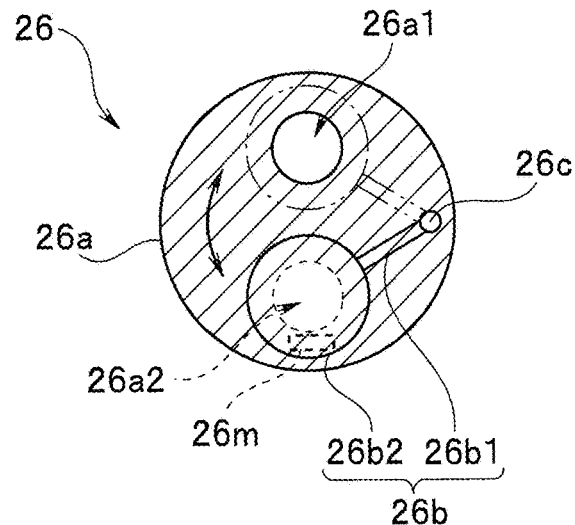
FIG. 3 is a configuration diagram of a mechanical shutter 26 according to the first embodiment of the present invention.

FIG. 3 is a configuration diagram of the mechanical shutter 26. The mechanical shutter 26 is provided with a circular aperture member 26a including two openings and a shielding member 26b.

The two openings 26a1 and 26a2 of the aperture member 26a constitute the apertures of the two optical paths of the right eye optical system 22R and the left eye optical system 22L respectively. The mechanical shutter 26 is arranged inside the optical adapter 10 so that the two circular openings 26a1 and 26a2 are disposed at the respective positions of the two optical paths.

Note that the aperture member 26a may also be constructed of two members: an aperture member including the opening 26a1 and an aperture member including the opening 26a2.

The shielding member 26b includes an arm 26b1 configured to be rotatable around a shaft of a shaft member 26c fixed to the aperture member 26a and a circular light-shielding plate 26b2 formed at a distal end of the arm 26b1. The shielding member 26b is provided with a magnet 26m.

As is shown by an arrow, the shielding member 26b is movable between a first position covering the opening 26a1 disposed in the optical path of the right eye optical system 22R and a second position covering the opening 26a2 disposed in the optical path of the left eye optical system 22L.

Through a magnetic field generated by a coil (not shown) in the optical adapter 10, the shielding member 26b having the magnet 26m can be located at either the first position or the second position. Movement of the shielding member 26b is controlled by a drive signal from the body section 2 being supplied to the coil through a signal line (not shown).

Figure 4:
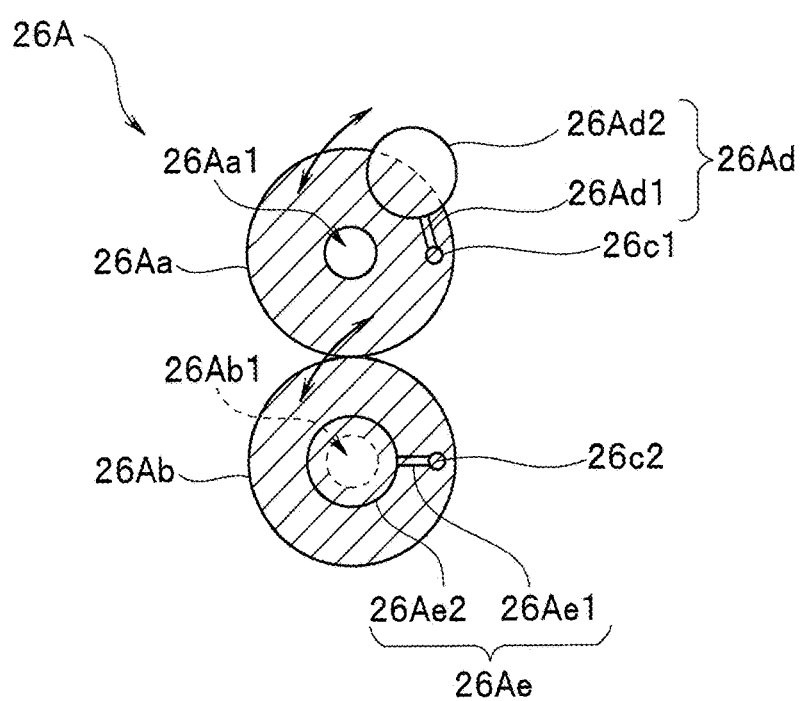
FIG. 4 is a configuration diagram of another example of the mechanical shutter according to the first embodiment of the present invention.

The configuration of the mechanical shutter 26 may be different from the configuration shown in FIG. 3. FIG. 4 is a configuration diagram in another example of the mechanical shutter. A mechanical shutter 26A includes two circular aperture members 26Aa and 26Ab. The two aperture members 26Aa and 26Ab include circular openings 26Aa1 and 26Ab1 respectively. The two aperture members 26Aa and 26Ab include shielding members 26Ad and 26Ae respectively.

The shielding member 26Ad includes an arm 26Ad1 configured to be rotatable around a shaft of a shaft member 26c1 fixed to the aperture member 26Aa and a circular light-shielding plate 26Ad2 formed at a distal end of the arm 26Ad1.

The shielding member 26Ae includes an arm 26Ae1 configured to be rotatable around a shaft of a shaft member 26c2 fixed to the aperture member 26Ab and a circular light-shielding plate 26Ae2 formed at a distal end of the arm 26Ae1.

Each of shielding members 26Ad and 26Ae is provided with a magnet (not shown).

An opening 26Aa1 of the aperture member 26Aa is disposed in the optical path of the right eye optical system 22R and an opening 26Ab1 of the aperture member 26Ab is disposed in the optical path of the left eye optical system 22L.

In the case of FIG. 4, a coil (not shown) is provided for each of the shielding members 26Ad and 26Ae and the two coils are driven so that the two shielding members 26Ad and 26Ae alternately cover their respective openings 26Aa1 and 26Ab1.

Thus, the mechanical shutter 26 may also be the mechanical shutter having the configuration shown in FIG. 4.

As shown in FIG. 2, the light incident on the right eye optical system 22R from the object passes through the opening 26a1 of the aperture member 26a arranged on the proximal end side of the right eye optical system 22R and is made incident on the image forming optical system 36. Similarly, though not shown in FIG. 2, the light incident on the left eye optical system 22L from the object passes through the opening 26a2 of the aperture member 26a disposed on the proximal end side of the left eye optical system 22L and is made incident on the image forming optical system 36.

As described above, the two optical path forming optical systems 22R and 22L, the image forming optical system 36 and the image pickup device 35 constitute the image pickup apparatus.

The center of the opening 26a1 of the aperture member 26a is not located on the optical axis of the right eye optical system 22R, but is deviated with respect to an optical axis OR of the right eye optical system 22R, toward the optical axis side of the image forming optical system 36, that is, the central axis O side of the image pickup device 35.

Similarly, the center of the opening 26a2 of the aperture member 26a is not located on the optical axis of the left eye optical system 22L either, but is deviated with respect to an optical axis OL of the left eye optical system 22L, toward the optical axis side of the image forming optical system 36, that is, the central axis O side of the image pickup device 35.

Figure 5:
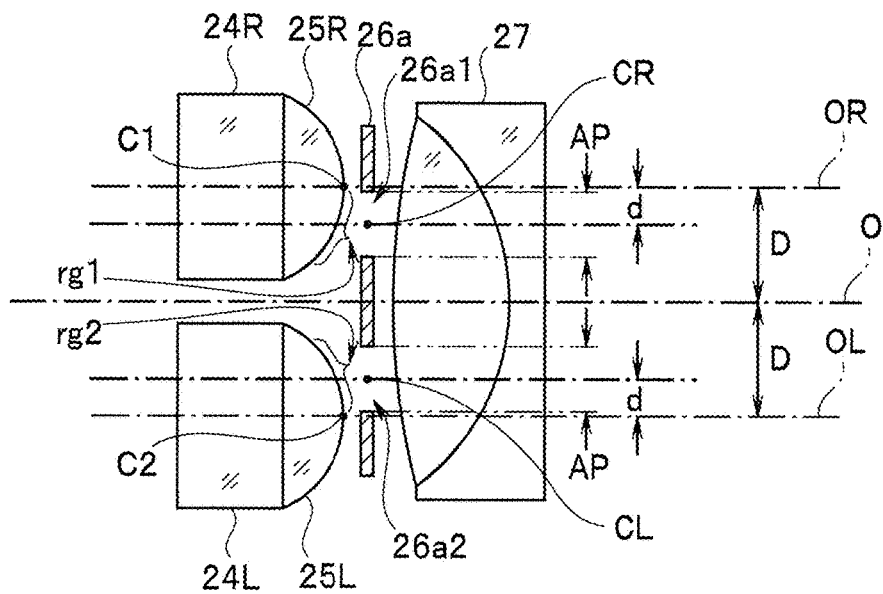
FIG. 5 is a diagram for describing a positional relationship between two centers of openings 26$a$1 and 26$a$2 of an aperture member 26$a$, and a central axis O of an image pickup device 35 according to the first embodiment of the present invention.

FIG. 5 is a diagram for describing a positional relationship between the two centers of the openings 26a1 and 26a2 of the aperture member 26a and the central axis O of the image pickup device 35. FIG. 5 illustrates the optical system viewed from a direction orthogonal to a parallax direction.

As shown in FIG. 5, although the optical axis OR of the right eye optical system 22R and the optical axis OL of the left eye optical system 22L are parallel to the central axis O of the image pickup device 35, the optical axis OR and the optical axis OL are respectively located at a predetermined distance D from the central axis O.

Furthermore, a center CR of the opening 26a1 of the aperture member 26a is not located on the optical axis OR of the right eye optical system 22R, but is deviated with respect to the optical axis OR of the right eye optical system 22R by a distance d toward the optical axis side of the image forming optical system 36, that is, the central axis O side of the image pickup device 35. Similarly, a center CL of the opening 26a2 of the aperture member 26a is not located on the optical axis OL of the left eye optical system 22L, but is deviated with respect to the optical axis OL of the left eye optical system 22L by a distance d toward the optical axis side of the image forming optical system 36, that is, the central axis O side of the image pickup device 35.

That is, the aperture member 26a includes the opening 26a1 that transmits the light emitted from the convex power section 25R and the opening 26a2 that transmits the light emitted from the convex power section 25L, the center CR of the first opening 26a1 is located on the optical axis O side of the image forming optical system 36 with respect to the optical axis OR of the right eye optical system 22R and the center CL of the second opening 26a2 is located on the optical axis O side of the image forming optical system 36 with respect to the optical axis OL of the left eye optical system 22L.

The openings 26a1 and 26a2 are each formed in the aperture member 26a so and not to overlap with the central axis O. An inner diameter of each opening 26a1 and 26a2 is AP.

Therefore, the distance d satisfies $0<d<(D-(AP/2))$.

That is, when the distance between each optical axis OR or optical axis OL and the optical axis O of the image forming optical system 36 is assumed to be D, the inner diameter of the first and the second openings 26a1 and 26a2 is assumed to be AP, and the distance between the optical axis OR and the center of the opening 26a1 or the distance between the optical axis OL and the center of the opening 26a2 is assumed to be d, the distance d satisfies $0<d<(D-(AP/2))$.

Note that the openings 26a1 and 26a2 have the same inner diameter AP, but the openings may also have different inner diameters.

Hereinafter, the optical path of the right eye optical system 22R will be described. The optical path of the left eye optical system 22L is axially symmetric to the optical path of the right eye optical system 22R with respect to the central axis O. The convex power section 25R and the convex power section 25L are arranged axially symmetrically with respect to the optical axis O of the image forming optical system.

A center C1 of the convex power section 25R is located on the optical axis OR of the right eye optical system 22R. The convex power section 25R has a function of condensing the light passing through the right eye optical system 22R.

Light emitted from the convex power section 25R passes through the opening 26a1 of the aperture member 26a. A luminous flux emitted from the opening 26a1 passes through the image forming optical system 36 and is condensed on the image pickup surface 35b of the image pickup device 35.

At this time, the center CR of the opening 26a1 is not located on the optical axis of the right eye optical system 22R, but is deviated with respect to the optical axis OR of the right eye optical system 22R toward the central axis O side of the image pickup device 35. Therefore, in FIG. 5, light from a region rg1 on the central axis O side of the convex power section 25R of the light emitted from the convex power section 25R mainly passes through the opening 26a1. In FIG. 5, the region rg1 is a lower region of the convex power section 25R.

The center CR of the opening 26a1 is not located on the optical axis OR of the right eye optical system 22R, but is located on the central axis O side of the optical axis OR with respect to the optical axis OR of the right eye optical system 22R, whereas the light from the right eye optical system 22R is refracted in the region rg1 and emitted toward the image forming optical system 36.

The light refracted in the region rg1 on the central axis O side of the convex power section 25R passes through the opening 26a1 of the aperture member 26a and is made incident on the image forming optical system 36.

The optical path along which light is made incident on the image pickup device 35 will be described by tracing back the optical path.

A central luminous flux CB directed from the image pickup device 35 toward the opening 26a1 shifted by (D-d) from the central axis O passes through the region rg1 of the convex power section 25R. Not only the central luminous flux CB but also an off-axis luminous flux MB passes through the region rg1.

When passing through the region rg1, the central luminous flux CB and the off-axis luminous flux MB receive effects of condensing action and refraction action, pass through the right eye optical system 22R while increasing the height of each luminous flux and are made incident on the plano-concave lens 23R.

Since the plano-concave lens 23R covers a wide angle of view and emits a luminous flux of a large height to the object side, a large parallax amount is secured.

The same applies to the left eye optical system 22L. In FIG. 5, light is refracted in a region rg2 on the central axis O side of the convex power section 25L.

As described above, the center CR of the opening 26a1 of the aperture member 26a and the center CL of the opening 26a2 are shifted from the optical axis OR of the right eye optical system 22R and the optical axis OL of the left eye optical system 22L respectively toward the central axis O side using the refraction action of each convex power section 25R or 25L. This makes it possible to reduce the outside diameter of the common image forming optical system 36, providing an image pickup apparatus suitable for mounting, for example, to an insertion portion of an endoscope, a diameter of which is expected to be reduced.

Generally, each pixel of a color filter on a light receiving surface of an image pickup device is disposed offset with respect to a pixel region of the corresponding image pickup device so as to receive the largest possible amount of light in each pixel region of the image pickup device in accordance with the angle of incidence of light. Therefore, light passing through two optical paths has a large height of off-axis light beam at positions away from the central axis of the image pickup device, more likely to generate luminance shading, and color shading may also occur depending on the image pickup device.

Especially when light beams passing through two optical paths are caused to form images on the image pickup surface of the image pickup device, the luminous flux passing through each optical path spreads after passing through the corresponding aperture, and so the height of off-axis light beam farthest from the central axis of the image pickup device increases, that is, increases the distance from the central axis of the light passing through the point farthest from the central axis of the image pickup device.

However, according to the present embodiment, the center CR of the opening 26a1 of the aperture member 26a and the center CL of the opening 26a2 are deviated toward the central axis O side from the optical axis OR of the right eye optical system 22R and the optical axis OL of the left eye optical system 22L respectively. Therefore, the two luminous fluxes from the two openings 26a1 and 26a2 are made incident on the image forming optical system 36 from the regions rg1 and rg2 close to the central axis O. As a result, the height of the off-axis light beam farthest from the central axis of the image pickup device passing through the image forming optical system 36 becomes lower than in prior arts and luminance shading is less likely to occur. In other words, the angle of incidence of the image pickup device 35 on the image pickup surface 35b becomes an angle at which shading is less likely to occur than in prior arts.

Furthermore, as shown in FIG. 5, the luminous flux from the opening 26a1 passes through the upper part of the image forming optical system 36 (part apart from the central axis O), but since the light from the right eye optical system 22R passes through the lower part (part on the central axis O side) of the convex power section 25R, an effect of canceling eccentric aberration is generated. An effect of canceling out eccentric aberration is also generated for the light from the left eye optical system 22L.

As described above, according to the aforementioned embodiment, it is possible to provide an image pickup apparatus including two optical systems having parallax capable of reducing the diameter of the objective optical system and an endoscope apparatus using the image pickup apparatus.

Furthermore, according to the aforementioned embodiment, it is possible to inhibit the occurrence of luminance shading or the like.

Note that as a modification, the optical axis of the plano-concave lens 23R need not be aligned with the optical axis OR of the right eye optical system 22R, and in the same way, the optical axis of the plano-concave lens 23L need not be aligned with the optical axis OL of the left eye optical system 22L.

Figure 6:
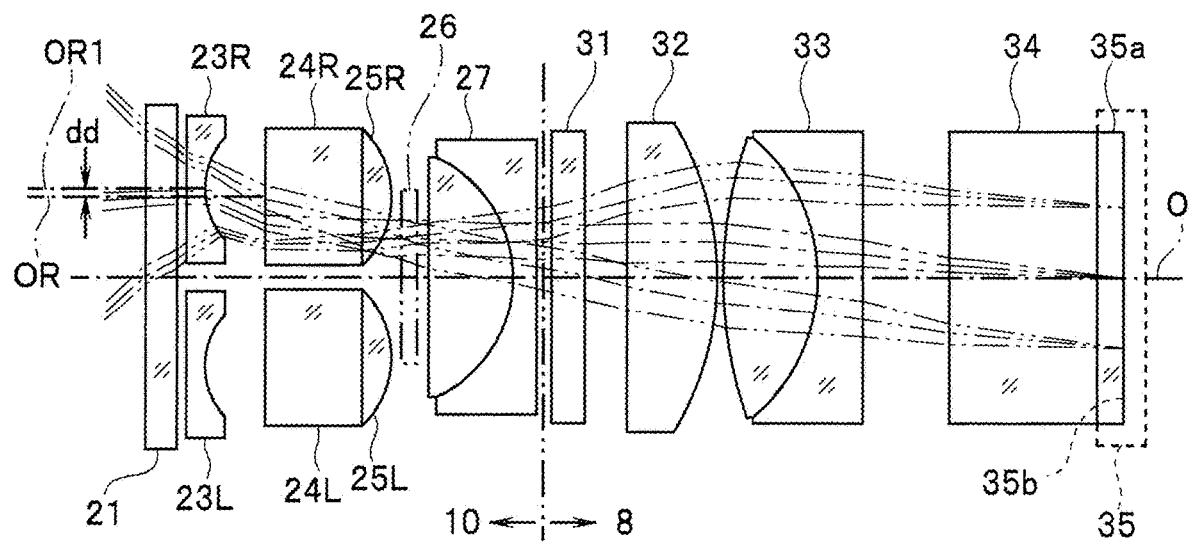
FIG. 6 is a configuration diagram of an optical system of a distal end portion 8, with an optical adapter 10 attached at a distal end according to modification 1 of the first embodiment of the present invention.

FIG. 6 is a configuration diagram of the optical system of a distal end portion 8 with an optical adapter 10 attached at a distal end according to modification 1 of the first embodiment. FIG. 6 illustrates only an optical path passing through the right eye optical system 22R. As shown in FIG. 6, an optical axis OR1 of the plano-concave lens 23R is deviated by a distance dd with respect to the optical axis OR of the plano-convex lens 24R in a direction away from the central axis O.

That is, the optical axis OR1 of the plano-concave lens 23R is deviated with respect to the optical axis OR toward a side opposite to the optical axis O of the image forming optical system 36 and the optical axis of the plano-concave lens 23L is also deviated with respect to the optical axis OL toward a side opposite to the optical axis O of the image forming optical system 36.

As a result, a larger parallax amount can be secured.

Second Embodiment

In the image pickup apparatus of the endoscope of the first embodiment, two light beams passing through the left and right objective optical systems form images in a common region on the image pickup surface of the image pickup device, whereas in an image pickup apparatus of an endoscope of the present embodiment, two light beams passing through the left and right objective optical systems form images in two different regions on the image pickup surface of the image pickup device.

The endoscope of the present embodiment has substantially the same configuration as the configuration of the endoscope of the first embodiment shown in FIG. 1. Therefore, in the present embodiment, the same components as the components in the first embodiment are assigned the same reference numerals and description of the components is omitted, and only different components will be described.

Figure 7:
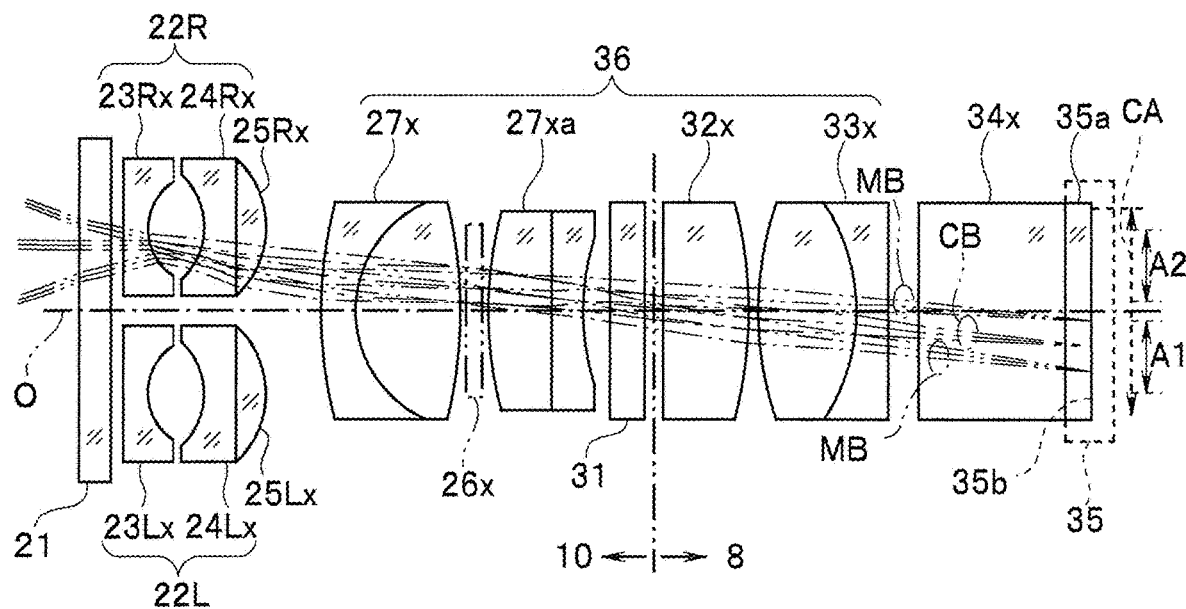
FIG. 7 is a configuration diagram of an optical system of a distal end portion 8, with an optical adapter 10 attached at a distal end according to a second embodiment of the present invention.

FIG. 7 is a configuration diagram of an optical system of a distal end portion 8 with an optical adapter 10 attached at the distal end according to the present embodiment.

A cover glass 21 is provided at a distal end of the optical adapter 10. Right and left objective optical systems, that is, a right eye optical system 22Rx and a left eye optical system 22Lx are arranged behind the cover glass 21 in the optical adapter 10.

The right eye optical system 22Rx includes a plano-concave lens 23Rx and a concave-convex lens 24Rx in order from the distal end. The proximal end portion of the concave-convex lens 24Rx constitutes a convex power section 25Rx.

The left eye optical system 22Lx includes a plano-concave lens 23Lx and a concave-convex lens 24Lx in order from the distal end. The proximal end portion of the concave-convex lens 24Lx constitutes a convex power section 25Lx.

Note that the concave-convex lenses 24Rx and 24Lx may be plano-convex lenses.

On the proximal end side of the right eye optical system 22Rx and the left eye optical system 22Lx, a bonded convex lens 27x formed of a plurality of lenses, an aperture member 26x, a bonded convex lens 27xa formed of a plurality of lenses and a cover glass 31 are arranged in order from the distal end toward the proximal end in the optical adapter 10.

The distal end portion 8 is arranged with a plano-convex lens 32x and a bonded convex lens 33x formed of a plurality of lenses in order from the distal end. On the proximal end side of the bonded convex lens 33x, an image pickup device 35 is arranged, to which a protective glass section 34x formed of a plurality of glass sheets is fixed.

The bonded convex lenses 27x and 27xa, the plano-convex lens 32x and the bonded convex lens 33x constitute an image forming optical system 36 common to the right eye optical system 22R and the left eye optical system 22L. That is, light emitted from the right eye optical system 22R and light emitted from the left eye optical system 22L pass through two openings of the aperture member 26x respectively and are made incident on the image forming optical system 36.

The image forming optical system 36 is configured to cause the emitted light from the right eye optical system 22R and the emitted light from the left eye optical system 22L to form images in two different regions on the image pickup surface of the image pickup device 35.

The aperture member 26x has a configuration similar to the configuration of the aperture member 26a described in FIG. 3 and includes an opening 26a1 that transmits light passing through the right eye optical system 22R and an opening 26a2 that transmits light passing through the left eye optical system 22L. Therefore, although the image pickup device 35 simultaneously receives the light passing through the right eye optical system 22R and the light passing through the left eye optical system 22L, the light passing through the right eye optical system 22R and the light passing through the left eye optical system 22L form images in two different image pickup regions A1 and A2 on the image pickup surface of the image pickup device 35.

Note that FIG. 7 illustrates only the optical paths of the central luminous flux CB and the two off-axis luminous fluxes MB of the light passing through the right eye optical system 22R.

The two openings 26a1 and 26a2 constitute respective apertures of the two optical paths of the right eye optical system 22R and the left eye optical system 22L. The aperture member 26x is arranged in the optical adapter 10 so that two circular openings 26a1 and 26a2 are arranged at the respective positions of the two optical paths.

As shown in FIG. 7, the light incident on the right eye optical system 22R from the object passes through the opening 26a1 of the aperture member 26x arranged on the proximal end side of the right eye optical system 22R. Similarly, though not shown in FIG. 7, the light incident on the left eye optical system 22L from the object passes through the opening 26a2 of the aperture member 26x disposed on the proximal end side of the left eye optical system 22L.

A center CR of the opening 26a1 of the aperture member 26x is not located on the optical axis OR of the right eye optical system 22R, but is deviated with respect to the optical axis OR of the right eye optical system 22R toward the optical axis of the image forming optical system 36, that is, the central axis O side of the image pickup device 35.

Similarly, a center CL of the opening 26a2 of the aperture member 26x is not located on the optical axis OL of the left eye optical system 22L, but is deviated with respect to the optical axis OL of the left eye optical system 22L toward the optical axis of the image forming optical system 36, that is, the central axis O side of the image pickup device 35.

Therefore, as in the case of the first embodiment, the two luminous fluxes from the right eye optical system 22R and the left eye optical system 22L are made incident on the image forming optical system 36 from regions rg1 and rg2 close to the central axis O.

The present embodiment provides effects similar to the effects of the first embodiment.

That is, using the refraction action of each convex power section 25Rx and 25Lx, the center CR of the opening 26a1 of the aperture member 26x and the center CL of the opening 26a2 are shifted to the central axis O side from the optical axis OR of the right eye optical system 22R and the optical axis OL of the left eye optical system 22L respectively. Therefore, it is possible to reduce the outer diameter of the common image forming optical system 36 and provide an image pickup apparatus suitable for mounting, for example, to an insertion portion of an endoscope, a diameter of which is expected to be reduced.

Furthermore, in the present second embodiment, the optical axis of the plano-concave lens 23Rx need not be aligned with the optical axis OR of the right eye optical system 22Rx, and similarly the optical axis of the plano-concave lens 23Lx need not be aligned with the optical axis OL of the left eye optical system 22Lx.

Figure 8:
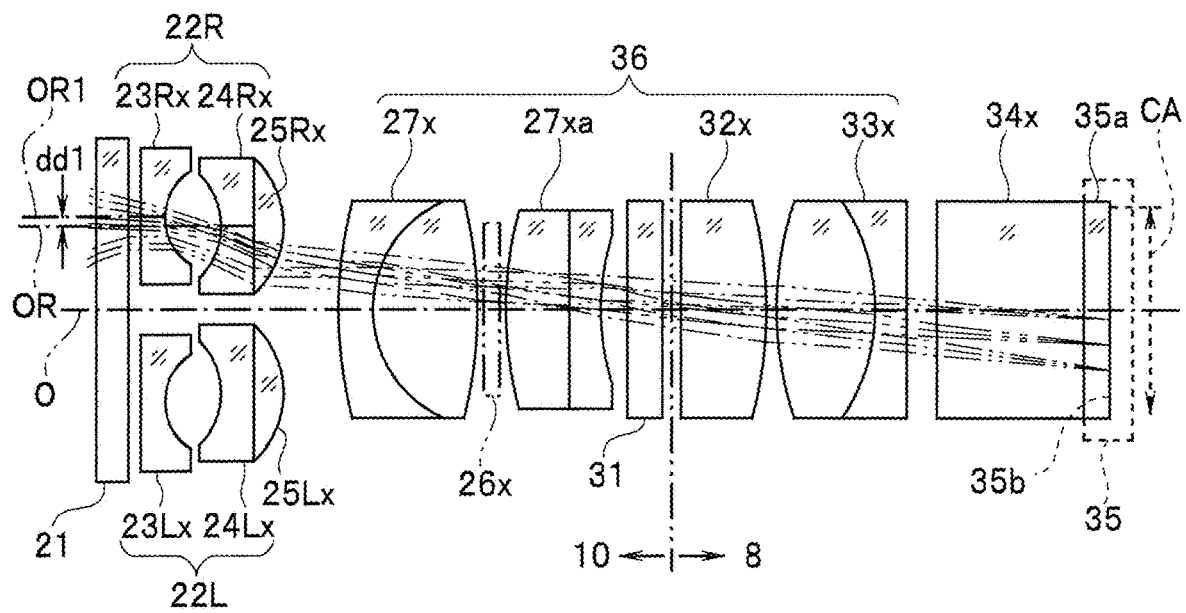
FIG. 8 is a configuration diagram of an optical system of a distal end portion 8, with an optical adapter 10 attached at a distal end according to modification 2 of the second embodiment of the present invention.

FIG. 8 is a configuration diagram of an optical system of a distal end portion 8 with an optical adapter 10 attached at the distal end according to modification 2 of the second embodiment. FIG. 8 illustrates only the optical path passing through the right eye optical system 22R. As shown in FIG. 8, an optical axis OR1 of the plano-concave lens 23Rx is shifted with respect to the optical axis OR of a concave-convex lens 24Rx by a distance dd1 in a direction away from the central axis O.

As a result, a larger parallax amount can be secured.

As described above, according to the aforementioned respective embodiments and the modifications, it is possible to implement an image pickup apparatus including two optical systems having parallax capable of reducing a diameter of an objective optical system and an endoscope apparatus using the image pickup apparatus.

Note that in the aforementioned respective embodiments and modifications, a prism may be added to secure a larger parallax amount.

Figure 9:
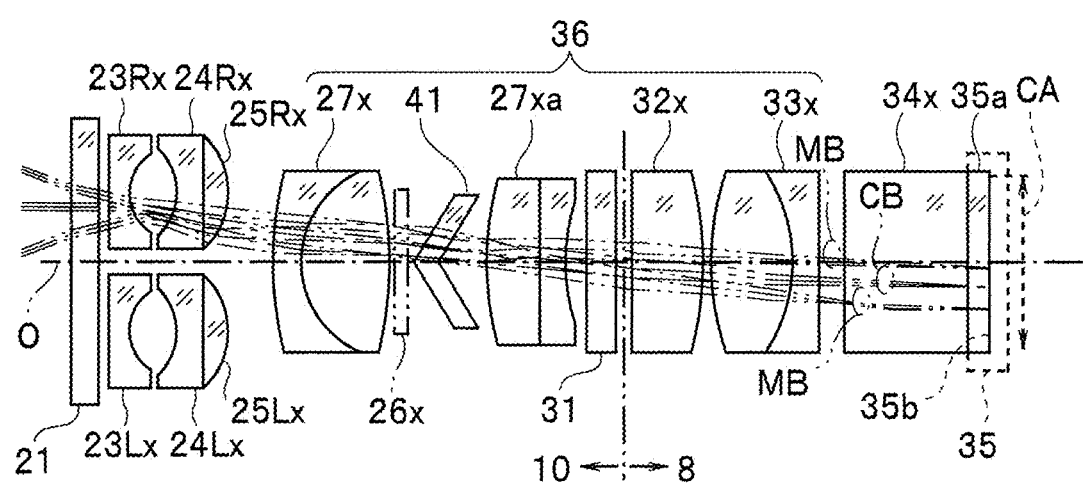
FIG. 9 is a configuration diagram of an optical system of a distal end portion 8, with an optical adapter 10, an image forming optical system of which includes a prism attached at a distal end according to modification 3 of the respective embodiments and modifications of the present invention.

FIG. 9 is a configuration diagram of an optical system of a distal end portion 8 with an optical adapter 10, an image forming optical system of which includes a prism attached at a distal end, according to modification 3 of the respective embodiments and modifications. FIG. 9 illustrates an optical system of the distal end portion 8 in the configuration of the second embodiment when the image forming optical system includes a prism.

As shown in FIG. 9, a prism 41 is arranged in the image forming optical system 36. The prism 41 is an axially symmetric wedge-shaped prism.

In FIG. 9, the optical axis of the plano-concave lens 23Rx is deviated with respect to the optical axis OR of the right eye optical system 22Rx toward the central axis (O) side of the image forming optical system and the optical axis of the plano-concave lens 23Lx is deviated with respect to the optical axis OL of the left eye optical system 22Lx toward the central axis (O) side of the image forming optical system, but the parallax amount of the two optical path forming optical systems is secured sufficiently by the prism 41.

In the first and second embodiments and the respective modifications, a larger parallax amount may be secured by disposing such a prism 41 in the image forming optical system 36.

The present invention is not limited to the aforementioned embodiments, but various changes, alterations or the like can be made without departing from the spirit and scope of the present invention.

What is claimed is:

1. An image pickup apparatus comprising:
   a first optical path forming optical system configured to form a first optical path;
   a second optical path forming optical system configured to form a second optical path;
   an image forming optical system disposed so as to receive emitted light from the first optical path forming optical system and emitted light from the second optical path forming optical system;
   a first convex power section including a convex portion, provided in the first optical path forming optical system and disposed so as to emit the emitted light from the first optical path forming optical system toward the image forming optical system;
   a second convex power section including a convex portion, provided in the second optical path forming optical system and disposed so as to emit the emitted light from the second optical path forming optical system toward the image forming optical system;
   an aperture member including a first opening configured to transmit the light emitted from the first convex power section and a second opening configured to transmit the light emitted from the second convex power section with a center of the first opening being located on an optical axis side of the image forming optical system with respect to a first optical axis of the first optical path forming optical system and a center of the second opening being located on an optical axis side of the image forming optical system with respect to a second optical axis of the second optical path forming optical system; and
   a bonded convex lens configured to allow the light emitted from the first convex power section and the light emitted from the second convex power section to pass in parallel,
   wherein the first optical path forming optical system, the second optical path forming optical system, the first convex power section, the second convex power section, the aperture member, and the bonded convex lens comprise an afocal optical system,
   the first convex power section is disposed such that the light from the first optical path forming optical system passes through a first part of the first convex power section and the first opening,
   the first part and the first opening are between the optical axis of the image forming optical system and the first optical axis,
   the first convex power section is configured such that the light passed through the first convex power section passes through a first side of the bonded convex lens with respect to the optical axis of the image forming optical system,
   the second convex power section is disposed such that the light from the second optical path forming optical system passes through a second part of the second convex power section and the second opening,
   the second part and the second opening are between the optical axis of the image forming optical system and the second optical axis,
   the second convex power section is configured such that the light passed through the second convex power section passes through a second side of the bonded convex lens with respect to the optical axis of the image forming optical system, and
   the second side is opposed to the first side across the optical axis of the image forming optical system.

2. The image pickup apparatus according to claim 1, wherein when a distance between each of the first optical axis and the second optical axis, and the optical axis of the image forming optical system is D, an inner diameter of the first and second opening is AP, and a distance between the first optical axis and the center of the first opening and a distance between the second optical axis and the center of the second opening is d, the distance d satisfies $0<d<(D-(AP/2))$.

3. The image pickup apparatus according to claim 1, wherein the first convex power section and the second convex power section are arranged axially symmetrically with respect to the optical axis of the image forming optical system.

4. The image pickup apparatus according to claim 1, further comprising:
   a first optical element provided on an incident light side of the first optical path forming optical system and including a concave surface; and
   a second optical element provided on an incident light side of the second optical path forming optical system and including a concave surface, wherein
   an optical axis of the first optical element is deviated toward a side opposite to the optical axis of the image forming optical system with respect to the first optical axis, and
   an optical axis of the second optical element is deviated toward a side opposite to the optical axis of the image forming optical system with respect to the second optical axis.

5. The image pickup apparatus according to claim 1, further comprising an image pickup device disposed at an image forming position of light emitted from the image forming optical system.

6. The image pickup apparatus according to claim 5, further comprising a shutter arranged between the first and second optical path forming optical systems and the image forming optical system, wherein
   the image forming optical system is configured to form images of the emitted light from the first optical path forming optical system and the emitted light from the second optical path forming optical system in a common region on an image pickup surface of the image pickup device, and
   the shutter is configured to operate so as to alternately radiate the emitted light from the first optical path forming optical system and the emitted light from the second optical path forming optical system onto the common region.

7. The image pickup apparatus according to claim 5, wherein the image forming optical system is configured to form images of the emitted light from the first optical path forming optical system and the emitted light from the second optical path forming optical system in two different regions on an image pickup surface of the image pickup device.

8. The image pickup apparatus according to claim 1, wherein the image forming optical system comprises a prism.

9. The image pickup apparatus according to claim 1, wherein the bonded convex lens is a part of the image forming optical system, and
no lenses are disposed between the first and second convex power sections and the bonded convex lens.

10. An endoscope apparatus comprising an image pickup apparatus, wherein
the image pickup apparatus comprises:
a first optical path forming optical system configured to form a first optical path;
a second optical path forming optical system configured to form a second optical path;
an image forming optical system disposed so as to receive emitted light from the first optical path forming optical system and emitted light from the second optical path forming optical system;
a first convex power section including a convex portion, provided in the first optical path forming optical system and disposed so as to emit the emitted light from the first optical path forming optical system toward the image forming optical system;
a second convex power section including a convex portion, provided in the second optical path forming optical system and disposed so as to emit the emitted light from the second optical path forming optical system toward the image forming optical system;
an aperture member including a first opening configured to transmit the light emitted from the first convex power section and a second opening configured to transmit the light emitted from the second convex power section with a center of the first opening being located on an optical axis side of the image forming optical system with respect to a first optical axis of the first optical path forming optical system and a center of the second opening being located on an optical axis side of the image forming optical system with respect to a second optical axis of the second optical path forming optical system; and
a bonded convex lens configured to allow the light emitted from the first convex power section and the light emitted from the second convex power section to pass in parallel,
wherein the first optical path forming optical system, the second optical path forming optical system, the first convex power section, the second convex power section, the aperture member, and the bonded convex lens comprise an afocal optical system,
the first convex power section is disposed such that the light from the first optical path forming optical system passes through a first part of the first convex power section and the first opening,
the first part and the first opening are between the optical axis of the image forming optical system and the first optical axis,
the first convex power section is configured such that the light passed through the first convex power section passes through a first side of the bonded convex lens with respect to the optical axis of the image forming optical system,
the second convex power section is disposed such that the light from the second optical path forming optical system passes through a second part of the second convex power section and the second opening,
the second part and the second opening are between the optical axis of the image forming optical system and the second optical axis,
the second convex power section is configured such that the light passed through the second convex power section passes through a second side of the bonded convex lens with respect to the optical axis of the image forming optical system, and
the second side is opposed to the first side across the optical axis of the image forming optical system.

11. An optical adapter configured to be attached to a distal end portion of an insertion portion of an endoscope, the optical adapter comprising:
a first optical path forming optical system configured to form a first optical path;
a second optical path forming optical system configured to form a second optical path;
a first convex power section including a convex portion, provided in the first optical path forming optical system and disposed so as to emit the emitted light from the first optical path forming optical system toward an image forming optical system;
a second convex power section including a convex portion, provided in the second optical path forming optical system and disposed so as to emit the emitted light from the second optical path forming optical system toward the image forming optical system;
an aperture member including a first opening configured to transmit the light emitted from the first convex power section and a second opening configured to transmit the light emitted from the second convex power section with a center of the first opening being located on an optical axis side of the image forming optical system with respect to a first optical axis of the first optical path forming optical system and a center of the second opening being located on an optical axis side of the image forming optical system with respect to a second optical axis of the second optical path forming optical system; and
a bonded convex lens configured to allow the light emitted from the first convex power section and the light emitted from the second convex power section to pass in parallel,
wherein the first optical path forming optical system, the second optical path forming optical system, the first convex power section, the second convex power section, the aperture member, and the bonded convex lens comprise an afocal optical system,
the first convex power section is disposed such that the light from the first optical path forming optical system passes through a first part of the first convex power section and the first opening,
the first part and the first opening are between the optical axis of the image forming optical system and the first optical axis,
the first convex power section is configured such that the light passed through the first convex power section passes through a first side of the bonded convex lens with respect to the optical axis of the image forming optical system,
the second convex power section is disposed such that the light from the second optical path forming optical system passes through a second part of the second convex power section and the second opening,
the second part and the second opening are between the optical axis of the image forming optical system and the second optical axis, the second convex power section is configured such that the light passed through the second convex power section passes through a second side of the bonded convex lens with respect to the optical axis of the image forming optical system, the second side is opposed to the first side across the optical axis of the image forming optical system, and the bonded convex lens comprises a part of the image forming optical system configured to form an image of light from an object on an image pickup surface of an image pickup device provided in the distal end portion, when the optical adapter is attached to the distal end portion.

* * * * *